US010448902B2

(12) United States Patent
Zoccatelli

(10) Patent No.: US 10,448,902 B2
(45) Date of Patent: Oct. 22, 2019

(54) METHOD AND APPARATUS FOR ACQUIRING PANORAMIC AND CBCT VOLUMETRIC RADIOGRAPHIES

(71) Applicant: Giacomo Zoccatelli, Negrar (IT)

(72) Inventor: Giacomo Zoccatelli, Negrar (IT)

(73) Assignee: CEFLA SOCIETÁ COOPERATIVA, Imola (IT)

( * ) Notice: Subject to any disclaimer, the term of this patent is extended or adjusted under 35 U.S.C. 154(b) by 537 days.

(21) Appl. No.: 15/199,134

(22) Filed: Jun. 30, 2016

(65) Prior Publication Data

US 2017/0007191 A1  Jan. 12, 2017

(30) Foreign Application Priority Data

Jul. 2, 2015  (IT) .......................... 102015000029774

(51) Int. Cl.
*A61B 6/03*  (2006.01)
*A61B 6/00*  (2006.01)
*A61B 6/04*  (2006.01)

(52) U.S. Cl.
CPC ................ *A61B 6/032* (2013.01); *A61B 6/04* (2013.01); *A61B 6/4085* (2013.01); *A61B 6/4441* (2013.01); *A61B 6/501* (2013.01); *A61B 6/505* (2013.01)

(58) Field of Classification Search
CPC ........... A61B 6/027; A61B 6/032; A61B 6/04; A61B 6/0421; A61B 6/102; A61B 6/14; A61B 6/4085; A61B 6/4441; A61B 6/501; A61B 6/505

See application file for complete search history.

(56) References Cited

U.S. PATENT DOCUMENTS

| 2009/0168966 | A1 | 7/2009 | Suzuki | |
|---|---|---|---|---|
| 2013/0089177 | A1* | 4/2013 | Baldini | A61B 6/14 378/39 |
| 2014/0328446 | A1* | 11/2014 | Sugihara | A61B 6/032 378/4 |

FOREIGN PATENT DOCUMENTS

| EP | 2210559 | 7/2010 |
|---|---|---|
| EP | 2774542 | 9/2014 |
| JP | 2013135765 | 7/2013 |

* cited by examiner

*Primary Examiner* — Chih-Cheng Kao
(74) *Attorney, Agent, or Firm* — Themis Law

(57) ABSTRACT

Method and apparatus for acquiring volumetric CBCT radiographies in an apparatus having a rotary supporting arm, at the ends of which at least an X-ray source and at least an X-ray sensor are positioned, the supporting arm rotating the at least one source and the at least one sensor around a patient. The method includes the steps of positioning a patient on the positioning device, and acquiring a CBCT image through a trajectory having an angular extension lower than 360°, wherein the rotation center of the trajectory of the X-ray sensor is never on the median sagittal plane defined by the patient positioned inside the apparatus and the trajectory is not symmetric to any of the possible sagittal planes of the patient.

11 Claims, 3 Drawing Sheets

METHOD AND APPARATUS FOR ACQUIRING PANORAMIC AND CBCT VOLUMETRIC RADIOGRAPHIES

FIELD OF THE INVENTION

The present invention refers to the technical field of extraoral dental radiography, and in particular to an apparatus capable of acquiring, in an alternate way, panoramic radiographies, volumetric radiographies with cone beam technique of facial bones, and optionally cranial teleradiographies. More particularly, the invention refers to a method and an apparatus for acquiring panoramic acquisitions (PAN) and volumetric acquisitions (CBCT) without the need of a device alternating the PAN sensor and the CBCT sensor.

BACKGROUND OF THE INVENTION

All these types of radiographies are well known in the art.

Panoramic radiography (PAN, also known as orthopantomography) produces a radiographic image of a curved plan approximating patient jaws, with blurring of the anatomical structures laying outside a narrow layer around the predesigned curved plane.

Cone beam volumetric radiography (also known as CBCT) is the acquisition, from different projection angles, of a series of two-dimensional radiographic images, which will be processed post-acquisition to reconstruct three-dimensional volumes.

Teleradiography (also known as CEPH) is a projective radiographic technique, producing radiographic images of the skull or of other anatomical areas from different projections, with minimum magnification and geometrical distortion. Usually two perspectives are represented, latero-lateral and antero-posterior.

For at least 10 years extraoral apparatuses have been known that produce PAN and CBCT images using a single source of X-rays and an alternating device which opposes a PAN sensor or a CBCT sensor to the X-ray source in an alternate way. An example of such known apparatus is described in patent EP2578157B1 of the same applicant.

The alternating device is needed in that the sensors for PAN and CBCT acquisitions are different; moreover, the distance X-ray source-sensor is not the same for PAN and CBCT acquisitions. As a matter of fact, in the panoramic acquisition the PAN sensor is usually at a distance comprised between 500 and 580 mm from the X-ray source, while the CBCT sensor in the volumetric CBCT radiography is usually positioned at distances comprised between 600 and 700 mm. Generally, for teleradiographic acquisitions, the distance X-ray source-sensor is around 1400-1600 mm.

Many of the apparatuses of the known art have three degrees of freedom or axes of movement: a rotation movement around a rotation axis R, and two translational movements along two directional axes, which are not parallel to each other, are preferably orthogonal and are called X and Y axes. Said translational movements allow moving the rotation axis R inside an XY plane. However, also apparatuses having only two degrees of freedom of movement are known: generally, these apparatuses allow a rotation around R axis and a translation along a directional axis, typically the Y axis. In the field of apparatuses capable of acquiring CBCT images only, apparatuses having only one degree of freedom are known, i.e. having a rotation around a R rotation axis.

Typically, with reference to FIG. 1, the R axis is a rotation axis of the arm carrying the X-ray source and sensor, and is parallel to the vertical axis of the apparatus. Translation X and Y axes are in the horizontal plane, or anyway in a plane perpendicular to R rotation axis; they are visible in FIGS. 2 and 3.

Apparatuses for the acquisition of panoramic and/or CBCT and/or CEPH apparatuses having only two degrees of freedom are available on the market, wherein said two degrees of freedom are a first R rotation axis, which can in turn be moved along a circular path around a rotation axis that is parallel and non-coincident.

Recently a new type of sensor has appeared on the market: a bi-dimensional (having two similar dimensions) X-ray sensor for CBCT acquisitions related to a selection of adjacent pixels, positioned inside a rectangle, which is wide about a few tens of pixels and as high as the entire sensor, or anyway at least about a thousand pixels. This new bi-dimensional sensor can be used for acquiring PAN images and has the peculiarity that the PAN selection of pixels can acquire images at a frequency much higher than that needed for a CBCT acquisition. The sensor used in CBCT mode (i.e. with its whole surface) reaches usually an acquisition frequency of about 30 frames/sec, while, when used in PAN mode, the above-described rectangular PAN selection only reaches an acquisition frequency of 100-200 frames/sec.

Today, when using this sensor, the panoramic image must be reconstructed a posteriori integrating the images obtained by the sensor.

PAN acquisitions are made on an angle smaller than 360°, generally around 220°; CBCT acquisitions are made normally on 360°, but can be performed even on a smaller angle (typically about 200°).

Document EP2774542 disclosed a dental radiographic device capable of carrying out CT imaging and PAN imaging. According to this document, a revolving arm carrying at the opposite ends the X-ray source and the X-ray sensor is configured to execute a rotation of 360° around the head of a patient. In order to be able to do this, the distance between sensor and source must be at least 600 mm or more. With a smaller distance, when imaging laterally positioned objects, there would exist a risk of collision between the source or the sensor and the head of the patient. The problem of reducing the overall dimensions of the apparatus is not addressed by this document. Likewise, the problem of avoiding conditions of risk of collisions between the source or the sensor and the head is suggested or discussed.

Document EP2210559 discloses a similar radiographic device which also carrie out CT imaging by a complete rotation around the patient head of the arm supporting the X-ray source and the X-ray sensor at his ends. The problem persists of reducing the dimensions of the apparatus by keeping the revolving arm a short as possible and at the same time avoiding potential collisions of the source or of the sensor with the head of the patient.

SUMMARY OF THE INVENTION

The present invention is directed to providing a method and an apparatus to perform alternately PAN or CBCT acquisition without the alternating mechanism described above, or without alternating devices described in patents of other manufacturers, or without mechanisms for adapting the X-ray source-sensor distance according to the acquisition to be performed, reducing as much as possible the length of the revolving arm and avoiding at the same time collisions of the source and of the sensor with the patient head while still providing high quality images.

This object is achieved by a method and an apparatus as described hereinafter. Advantageous embodiment and refinements are also described.

The apparatus according to the present invention has a single X-ray sensor, capable of performing PAN and CBCT acquisitions.

The distance X-ray source-sensor is the same for the two acquisitions, differently from what is usual in the known art. In the present invention, PAN acquisitions occur along the usual 220°, and the CBCT acquisition occurs along 200°.

Vertical planes through the body parallel to the median plane or the sagittal suture, dividing the body into unequal left and right portions are called sagittal planes. Among all sagittal planes, the plane positioned to divide the body into two halves having equal mass and approximately symmetrical and specular is called the median sagittal plane.

Today, radiography apparatus manufacturers tend to provide more and more compact apparatuses in order to save precious space inside the dental practice; this leads also to reducing the distance X-ray source-sensor.

Having a small distance between X-ray source and sensors is not a problem when acquiring a PAN image, in that the rotation center of FOV (Field Of View) is on the median sagittal plane of the patient; in this case, the sensor is in front of the patient and never reaches her/his back, where the collision with the patient's nape is unavoidable.

The problem of the collision between X-ray sensor and patient during a CBCT acquisition is not present when the center of the acquired volume is on the median sagittal plane of the patient (incisor teeth), while is present when lateral anatomic areas have to be acquired (molar teeth and temporomandibular joint). The problem is solved using a non-centered, non-symmetrical trajectory with respect to the patient so that the CBCT acquisition trajectory appears:

Not centered with respect to patient's head (in fact, the actual rotation center appears very near to a patient's ear, not passing through her/his median sagittal plane);

Not symmetrical with respect to any of the sagittal plane of the patient: the acquisition trajectory starts in front of the ear opposed to patient's area to be acquired and ends 200° after, slightly behind the patient's other ear.

This trajectory allows preventing collisions with the patient.

The advantages of the present invention include the simplification of the mechanical structure of the apparatus, which becomes much cheaper to produce, due to the use of one sensor only and the absence of the alternating device.

Moreover, having the distance between X-ray source and sensor be the same in the PAN and CBCT acquisition is an advantage in the CBCT acquisition, in that, with this distance, shorter than the standard distance, a larger field of view is obtained, because the magnifying factor of the anatomic structures on the sensor is nearer to 1.

BRIEF DESCRIPTION OF THE DRAWINGS

Further advantages and properties of the present invention are disclosed in the following description, in which exemplary embodiments of the present invention are explained in detail based on the drawings.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1:
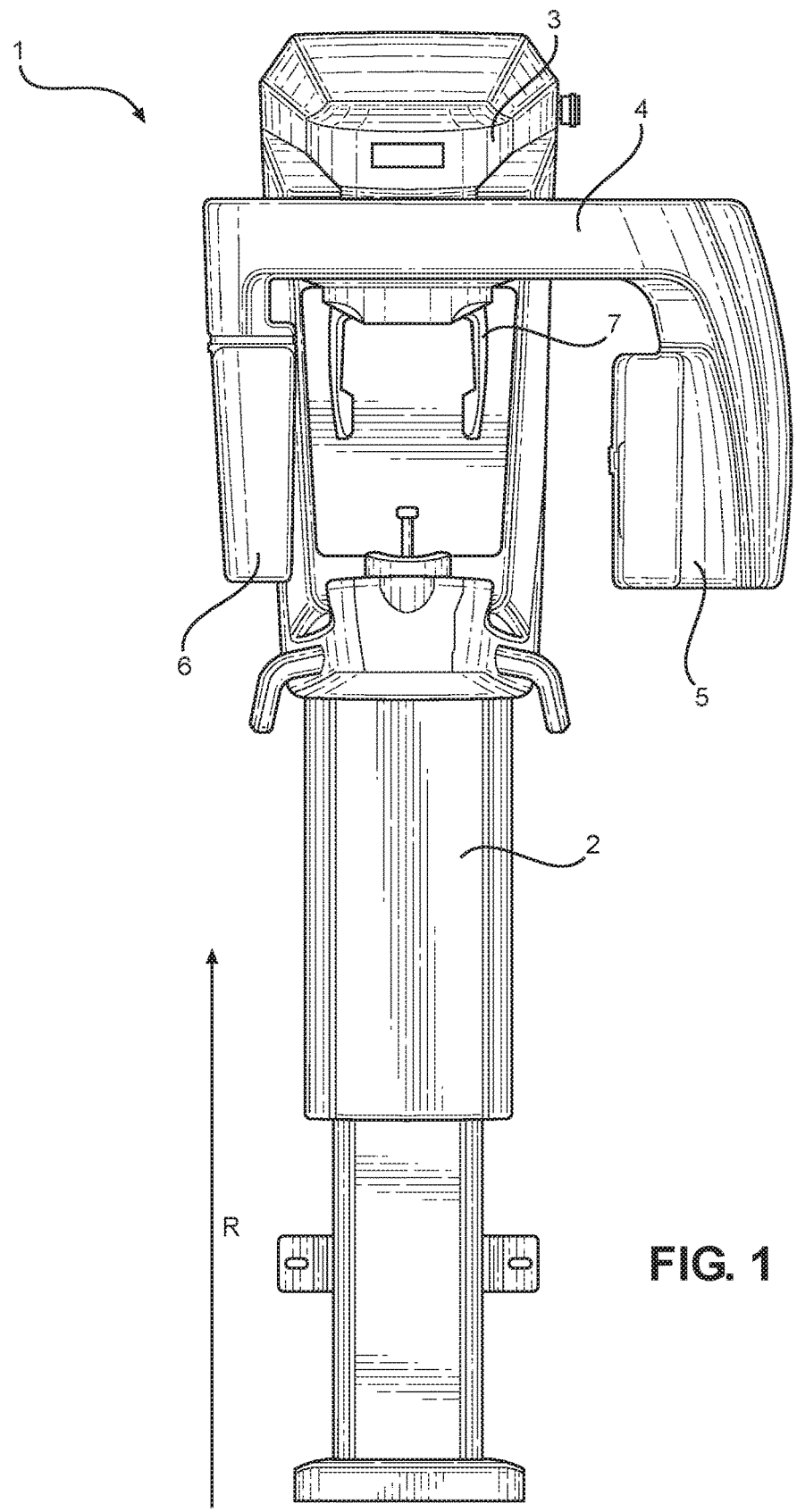
FIG. 1 is a front view of an apparatus according to the present invention.

In FIG. 1, numeral 1 indicates on the whole an extraoral radiographic apparatus capable of performing panoramic and CBCT radiographies according to the present invention. The apparatus 1 comprises a post 2 supporting a support 3. The support 3 supports a C-arm 4, which is fixed to the horizontal section of support 3. The C-arm 4 in turn supports at one of its ends an X-ray source 5, and at the opposed end an X-ray sensor 6. The support 3 is vertically movable in order to adjust it to the different heights of individual patients. Moreover, a device 7 for the positioning of the patient (not shown) is present, which is also fixed to support 3.

Figure 2:
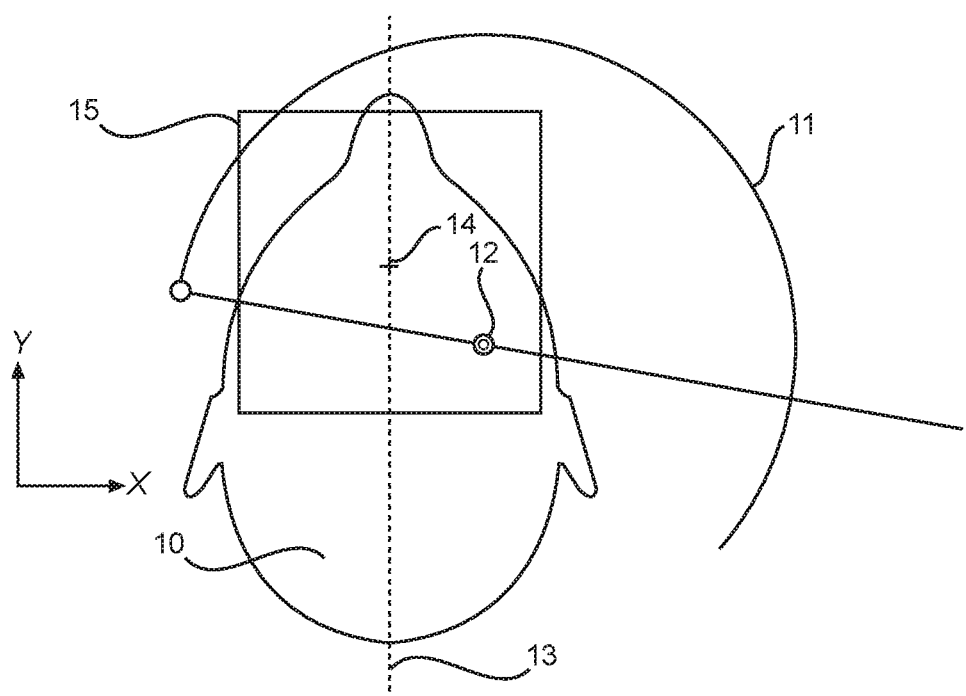
FIG. 2 is an exemplary top view of an example of a trajectory performed by the X-sensor during a CBCT acquisition in an apparatus allowing three degrees of freedom: one around the rotation axis of the C-arm 4, and the other two corresponding to the translation of said rotation axis in the plane perpendicular to said rotation axis and subtended by Cartesian X and Y axes.

FIG. 2 shows in a stylized way the head 10 of a patient in a top view. The trajectory followed by CBCT sensor during an acquisition is shown by line 11; numeral 12 indicates the center of rotation of trajectory 11. The dotted line 13 shows the median sagittal plane of the patient.

In an embodiment having three axes of movement X, Y, and R, the movement area 15 indicates the area, inside which the center of rotation R can be moved inside the XY plane. During a PAN acquisition the center of rotation 12 is moved according a pre-defined trajectory inside the square/rectangle 15.

Figure 3:
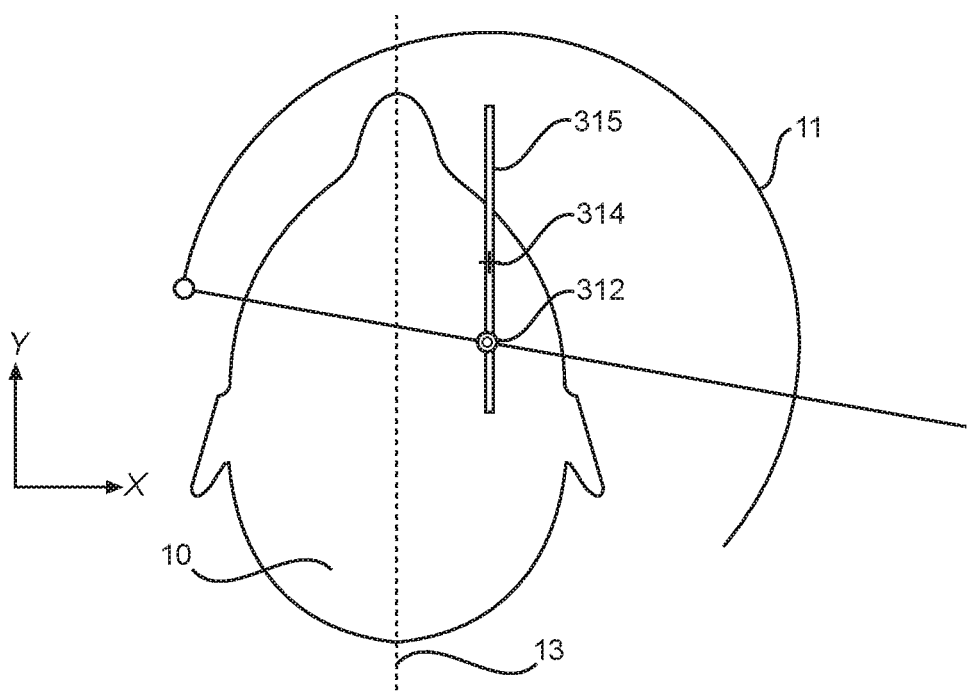
FIG. 3 is a top view similar to FIG. 2, wherein the apparatus has two degrees of freedom only, one around the rotation axis of the C-arm, and the other corresponding to the translation of said rotation axis along the Y axis, coincident with the horizontal plane and perpendicular to the rotation axis.

In an alternative embodiment having movements Y and R only, shown in FIG. 3, the movement area 15 is reduced to a segment 315 along the Y axis. For PAN acquisition the rotation R is moved only in the Y direction, while during all CBCT acquisitions the rotation axis R is kept steady in the same position. In this alternative embodiment, which is particularly inexpensive to produce due to the absence of the X motor, the trajectory shown in FIG. 3 can be obtained because the patient can be positioned so that her/his median sagittal plane does not pass in the vicinity of the movement area 15.

Figure 4:
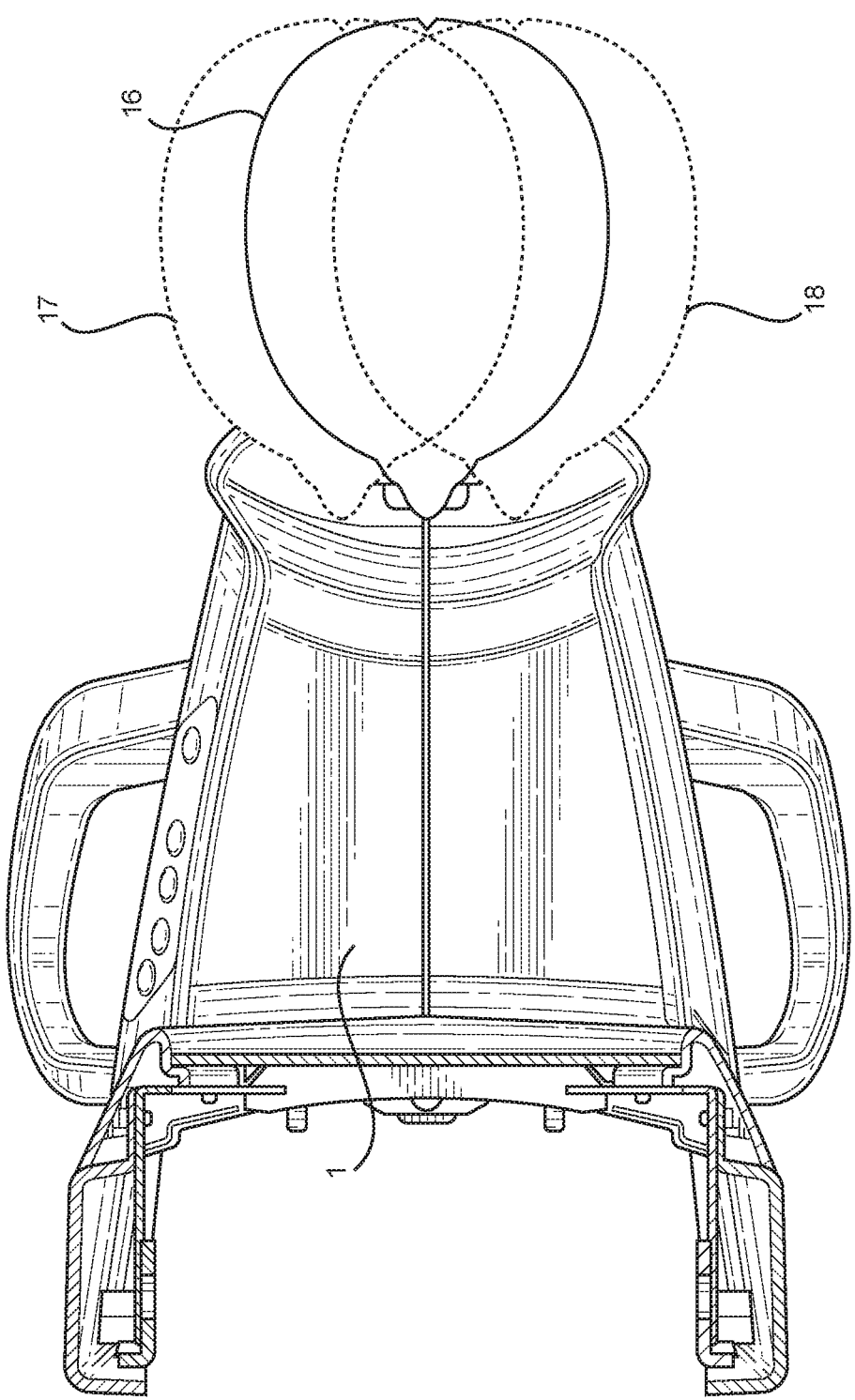
FIG. 4 is a top view of a patient positioned inside the apparatus.

FIG. 4 shows the positioning of patient's head 10 inside the apparatus 1, in different positions. The continuous line 16 indicates the patient's head, positioned in a symmetric way with respect to the apparatus 1 in all PAN trajectories in apparatuses provided with three and two axes of movement.

The patient is positioned so that her/his median sagittal plane crosses or passes near the area of movement 15 when the apparatus is provided with three axes of movement (X, Y, R), or when a CBCT acquisition is performed with an apparatus provided with two axes of movement (Y, R) and a central volume must be acquired (incisor teeth).

The patient is positioned so that her/his median sagittal plane does not pass near the movement area 15 when the apparatus 1 is provided with two axes of movement (Y, R) only, and a CBCT acquisition of the posterior teeth or of the temporomandibular joint must be performed. In FIG. 4, the discontinuous lines 17 and 18 indicate said non-symmetric positioning with respect to the apparatus 1.

It is apparent to the skilled person that the trajectory described in this application can be used also in apparatuses having two sensors, one PAN and one CBCT, or even in apparatuses capable of performing CBCT acquisitions only.

Moreover, it is apparent that when the apparatus is used to acquire teleradiographies, an arm (not shown) must be present having a length suitable for positioning the X-ray source at the necessary distance from the sensor (about 1400-1600 mm).

While the invention has been described with reference to the above embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

LISTING OF REFERENCE NUMERALS

1 Extraoral radiographic apparatus
2 Post
3 Support
4 C-arm
5 X-ray source
6 X-ray sensor
7 Device for positioning the patient
10 Patient's head
11 CBCT sensor trajectory
12, 312 Center of rotation
13 Median sagittal plane of the patient
14, 314 Center of the area of movement 15
15, 315 Area of movement
16 Symmetrically positioned patient
17 Asymmetrically positioned patient
18 Asymmetrically positioned patient

The invention claimed is:

1. A method of acquiring volumetric CBCT radiographies comprising:
providing an acquisition apparatus having a rotary supporting arm, wherein at least one X-ray source and at least one X-ray sensor are positioned at ends of the rotary supporting arm, and wherein the rotary supporting arm is configured to rotate the at least one X-ray source and the at least one X-ray sensor around a patient;
positioning a patient on a positioning device coupled to the apparatus; and
acquiring a CBCT image through a rotational trajectory of the rotary supporting arm having an angular extension less than 360°,
wherein a distance between the at least one X-ray source and the at least one X-ray sensor is between 500 to 580 mm,
wherein a rotation center of the trajectory of the X-ray sensor is never on a median sagittal plane defined by a patient positioned inside the apparatus,
wherein the trajectory of the X-ray sensor is not symmetric to any possible sagittal planes of the patient, and
wherein the rotational trajectory is caused to shift distally of the patient by causing the rotation center to shift distally of the patient during acquisition of the CBCT image and the rotary supporting arm to rotate for an angle sufficient to prevent a collision of the X-ray sensor with the patient's head.

2. The method according to claim 1, wherein the rotary supporting arm is provided with at least three degrees of freedom of movement (R, X, Y), said degrees of freedom consisting of a rotation around a rotation axis, and a translation of the rotation axis along at least two axes of directions perpendicular to each other, the two axes being contained in a plane perpendicular to the rotation axis.

3. The method according to claim 1, wherein the X-ray sensor, or the at least one X-ray sensor and the at least one X-ray source, have two degrees of freedom of movement (R, Y) consisting of a rotation around a rotation axis and a translation of the rotation axis, a directional axis perpendicular to the rotation axis, and wherein the patient is positioned so that her/his median sagittal plane is positioned beyond a pre-set minimal distance from a movement area during CBCT acquisition performed with the trajectory having the angular extension lower than 360°.

4. The method according to claim 3, wherein the CBCT acquisition trajectory has an angular extension of 200°.

5. The method according to claim 1, wherein the acquisition apparatus is a combined apparatus adapted to acquire panoramic and CBCT volumetric radiographies.

6. The method according to claim 5, wherein the acquisition apparatus is further adapted to acquire teleradiographic images.

7. An extraoral radiographic apparatus for acquiring CBCT images comprising:
a post coupled to a support;
a C-arm coupled to the support, the C-arm having at one end a X-ray source and at an opposed end a X-ray sensor, the C-arm being rotatable around a rotation axis (R), said rotation axis being moveable along an axial direction (Y) coincident with a plane that is perpendicular to the rotation axis, or movable along two axial directions (X, Y) perpendicular to each other and subtending a plane perpendicular to the rotation axis; and
a positioning device for a patient,
wherein the C-arm is configured to position the X-ray source and the X-ray sensor at a fixed distance between 500 to 580 mm,
wherein the C-arm is further configured to move along degrees of freedom that consist of rotation and translation along one or both of the axial directions to perform CBCT acquisition trajectories,
wherein the extraoral radiographic apparatus is configured to position the patient on the positioning device and acquire a CBCT image through a rotational trajectory of the C-arm having an angular extension less than 360°,
wherein a rotation center of the trajectory of the X-ray sensor is never on a median sagittal plane defined by a patient positioned inside the apparatus,
wherein the trajectory of the X-ray sensor is not symmetric to any possible sagittal planes of the patient, and
wherein the extraoral radiographic apparatus is configured to cause the trajectory of the X-ray sensor to shift distally of the patient by causing the rotation center to shift distally of the patient during acquisition of the CBCT image and the C-arm to rotate for an angle sufficient to prevent a collision of the X-ray sensor with the patient's head.

8. The extraoral radiographic according to claim 7, wherein the apparatus has only one sensor for acquiring PAN or CBCT images, the sensor having a selection of adjacent pixels with an acquisition frequency higher than an acquisition frequency of a sensor used for an entire scan surface.

9. The extraoral radiographic apparatus according to claim 7, wherein the apparatus has only one degree of freedom (Y) in addition to the rotation axis (R).

10. The extraoral radiographic apparatus according to claim 7, wherein the apparatus has two degrees of freedom (X, Y) in addition to the rotation axis (R).

11. The extraoral radiographic apparatus according to claim 7, wherein the extraoral radiographic apparatus is configured to acquire teleradiographies (CEPH) of the patient's skull.

* * * * *